(12) United States Patent
Amano et al.

(10) Patent No.: US 6,407,293 B1
(45) Date of Patent: Jun. 18, 2002

(54) PROCESS FOR PRODUCING 3-1-MENTHOXYPROPANE-1,2-DIOL

(75) Inventors: Akira Amano; Teruyoshi Akiyama; Takashi Miura; Toshimitsu Hagiwara, all of Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/962,122

(22) Filed: Sep. 26, 2001

(30) Foreign Application Priority Data

Oct. 23, 2000 (JP) ........................................ 2000-322287

(51) Int. Cl.[7] ........................ C07C 35/12; C07C 35/08; C07C 31/13
(52) U.S. Cl. ........................ 568/829; 568/822; 568/831
(58) Field of Search ................................ 568/829, 822, 568/831

(56) References Cited

U.S. PATENT DOCUMENTS 4,459,425 A    7/1984    Amano et al.
5,608,119 A    3/1997    Amano et al.

FOREIGN PATENT DOCUMENTS

| EP | 491 529 | 6/1992 |
|---|---|---|
| EP | 545 576 | 6/1993 |
| FR | 2479822 | 10/1981 |
| GB | 670 419 | 1/1939 |
| JP | 2000221 | 11/1990 |
| WO | WO 00/43340 | 7/2000 |

*Primary Examiner*—Samuel Barts
*Assistant Examiner*—Elvis O. Price
(74) *Attorney, Agent, or Firm*—Fitzpatrick, Cella, Harper & Scinto

(57) ABSTRACT

A process for producing highly pure 3-1-menthoxypropane-1,2-diol safely and efficiently, and an intermediate to be used in the process. 3-1-menthoxypropane-1,2-diol represented by the chemical formula (IV) is produced by adding 1-menthol to a 1,2-epoxy-3-halogenopropane represented by the following general formula (I) (wherein X represents a halogen atom) in an organic solvent in the presence of a Lewis acid to produce a novel 1-halogeno-3-1-menthoxypropan-2-ol represented by the following general formula (II), then, epoxidating it with a base in the presence of a phase transfer catalyst to produce a 1,2-epoxy-3-1-menthoxypropane represented by the chemical formula (III), and further hydrolyzing it.

11 Claims, No Drawings

PROCESS FOR PRODUCING 3-1-MENTHOXYPROPANE-1,2-DIOL

FIELD OF THE INVENTION

The present invention relates to a process for producing 3-1-menthoxypropane-1,2-diol useful as a cooling agent and a refrigerant, and to a 3-1-menthoxypropane derivative useful as an intermediate for producing 3-1-menthoxypropane-1,2-diol and a process for producing the same. According to the invention, highly pure 3-1-menthoxypropane-1,2-diol and 3-1-menthoxypropane derivatives useful as synthetic intermediates for 3-1-menthoxypropane-1,2-diol can be obtained safely and in high yields through simple operations.

BACKGROUND ART 3-1-Menthoxypropane-1,2-diol is a known compound as described in Japanese Patent Publication No. 48813/1986. 3-1-Menthoxypropane-1,2-diol is excellent in safety and also have a nature of imparting a cooling effect on skin and mucous membrane like 1-menthol. On the other hand, it is odorless unlike 1-menthol, and itself has no smell. Therefore, in the case of using 3-1-menthoxypropane-1,2-diol, a cooling effect can be imparted to a product without affecting the fragrance imparted to the product. Thus, utilizing the above characteristic of 3-1-menthoxypropane-1,2-diol, 3-1-menthoxypropane-1,2-diol has been blended with oral compositions such as tooth paste and chewing gum, and food and drink such as sherbet and hard candies, and further, it has been proposed to blend it with toilet articles such as cosmetics (Published Japanese Patent Application Nos. 25908/1985 and 208505/1988), an eye-pack agent (Published Japanese Patent Application No. 96403/1987) and a hair cosmetic (Published Japanese Patent Application No. 192312/1987), and others such as an aerosol composition for anti-inflammatory agents (Published Japanese Patent Application No. 264522/1988).

Processes for producing 3-1-menthoxypropane-1,2-diol which are known heretofore include (i) a process wherein 1-menthol is converted to the sodium salt with metal sodium or sodium hydride, then an allyl halide is reacted therewith to produce 3-1-menthoxypropan-1-ene, and it is oxidized using an organic peroxide to form an oxide, followed by hydrolysis (Japanese Patent Publication No. 48813/1986), and (ii) a process wherein 1-menthol is added to benzyl glycidyl ether in the presence of a Lewis acid to produce 1-benzyloxy-3-1-menthoxypropan-2-ol and it is subjected to hydrogenolysis in the presence of palladium-carbon catalyst to eliminate the benzyl group (Published Japanese Patent Application No. 82200/1995).

However, in the above conventional method (i), sodium salt of 1-menthol is produced with metal sodium or sodium hydride, and therefore there are problems of the risk of explosion and the generation of hydrogen gas. Furthermore, an intermediate of 3-1-menthoxypropan-1-ene is oxidized with an organic peroxide, and thus the risk of explosion also exists at the use. Accordingly, the process is not regarded as an industrially advantageous one and also some improvement is required from an economical point of view.

Moreover, since the above conventional process (ii) is a process for the purpose of synthesizing an optical isomer, it is necessary to use expensive benzyl glycidyl ether. In addition, 3-1-menthoxypropane-1,2-diol finally obtained contains about 10% of 2-1-menthoxypropane-1,3-diol as a by-product, so that the purification or fractionation by silica gel column chromatography or the like is necessary and thus it is difficult to obtain a large amount of highly pure 3-1-menthoxypropane-1,2-diol.

Furthermore, other than the above conventional processes, proposed is (iii) a process wherein 1-menthol is added to a 1,2-epoxy-3-halogenopropane such as epichlorohydrin in an aqueous solution in the presence of a base and a quaternary ammonium salt to produce 1,2-epoxy-3-1-menthoxypropane which is a synthetic intermediate for 3-1-menthoxypropane-1,2-diol [French Patent No. 2479822 (1981)]. However, 1,2-epoxy-3-halogenopropane such as epichlorohydrin is known to be unstable and prone to decompose in the presence of an acid or a base ["Kagaku Daijiten", p. 292, published by Tokyo Kagaku Dojin (1989)]. Therefore, in the case of this process where a 1,2-epoxy-3-halogenopropane is reacted in the presence of a base, the 1,2-epoxy-3-halogenopropane decomposes when the reaction takes a long period of time, so that it is difficult to synthesize 1,2-epoxy-3-1-menthoxypropane, and thus this process is not regarded as an advantageous process from industrial and economical viewpoints.

Furthermore, as the reaction between epichlorohydrin and an alcohol, proposed is (iv) a process for producing 1-allyloxy-3-chloro-2-propanol by reacting epichlorohydrin with allyl alcohol in the presence of an acidic catalyst (Published Japanese Patent Application No. 221/1990). In this conventional process (iv), however, the alcohol to be used in the reaction is only primary allyl alcohol and the application to a secondary alcohol, much less the addition reaction with menthol, is not reported.

In addition, as another conventional process, there is proposed (v) a process wherein an epihalohydrin is reacted with an alcohol in the presence of an acid catalyst, then the product is treated with an alkali to form a glycidyl ether through ring closure, and after hydrolysis, the reaction mixture is heated at 100 to 230° C. in the presence of a salt formed from a strongly basic compound and a weakly acidic compound to produce a glycerol ether (Published Japanese Patent Application No. 212114/2000). However, in order to decompose an organohalogen contained in hydrolyzate of the glycidyl ether, this process requires heating the reaction mixture at a high temperature of 100 to 230° C., especially 150 to 200° C. in the presence of a salt formed from a strongly basic compound and a weakly acidic compound, and thus is not an efficient process. Furthermore, the alcohol to be used in the process is a primary alcohol represented by the general formula: R—(OA)$_p$—OH (wherein R represents a saturated or unsaturated linear or branched hydrocarbon group having 1 to 36 carbon atoms, A represents an alkylene group having 2 to 4 carbon atoms, and p represents one number of 0 to 100), and the use of secondary alcohol is not disclosed, much less the use of menthol is not disclosed at all.

An object of the invention is to provide a process for producing highly pure 3-1-menthoxypropane-1,2-diol safely and in high yields through simple operations.

Other object of the invention is to provide an intermediate useful for obtaining highly pure 3-1-menthoxypropane-1,2-diol.

Still other object of the invention is to provide a process for producing intermediates useful for obtaining 3-1-menthoxypropane-1,2-diol efficiently.

SUMMARY OF THE INVENTION

The present inventors have extensively studied for achieving the above objects. As a result, a novel compound of a 1-halogeno-3-1-menthoxypropan-2-ol can be produced by adding 1-menthol to a 1,2-epoxy-3-halogenopropane in an organic solvent in the presence of a Lewis acid. And, as a result of further studies, they have found that the novel 1-halogeno-3-1-menthoxypropan-2-ol is chemically stable and can be stored by itself, and 1,2-epoxy-3-1-menthoxypropane, which is also an intermediate for obtaining 3-1-menthoxypropane-1,2-diol, is obtained at a high reaction rate and in high yields by further epoxidating the 1-halogeno-3-1-menthoxypropan-2-ol with a base in the presence of a phase transfer catalyst, and objective 3-1-menthoxypropane-1,2-diol is obtained conveniently in good yields and at a high purity by hydrolyzing the 1,2-epoxy-3-1-menthoxypropane. Based on these findings, they have accomplished the invention.

Namely, the invention relates to:

(1) a process for producing 3-1-menthoxypropane-1,2-diol, which comprises:

adding 1-menthol to a 1,2-epoxy-3-halogenopropane represented by the following general formula (I):

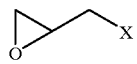

(I)

(wherein X represents a halogen atom), in an organic solvent in the presence of a Lewis acid to produce a 1-halogeno-3-1-menthoxypropan-2-ol represented by the following general formula (II):

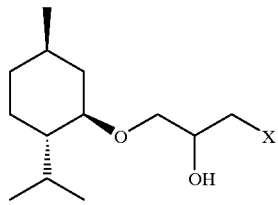

(II)

(wherein X represents a halogen atom), then, epoxidating it with a base in the presence of a phase transfer catalyst to produce a 1,2-epoxy-3-1-menthoxypropane represented by the following chemical formula (III):

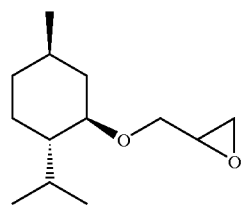

(III)

and further hydrolyzing it to produce 3-1-menthoxypropane-1,2-diol represented by the following chemical formula (IV).

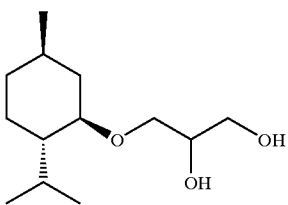

(IV)

And, the invention relates to:

(2) a process for producing 3-1-menthoxypropane-1,2-diol, which comprises:

epoxidating a 1-halogeno-3-1-menthoxypropan-2-ol represented by the following general formula (II):

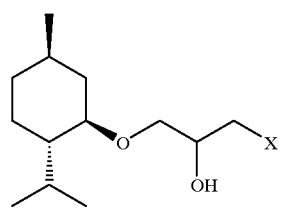

(II)

(wherein X represents a halogen atom), with a base in the presence of a phase transfer catalyst to produce a 1,2-epoxy-3-1-menthoxypropane represented by the following chemical formula (III):

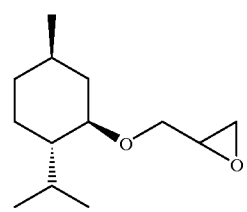

(III)

and further hydrolyzing it to produce 3-1-menthoxypropane-1,2-diol represented by the following chemical formula (IV).

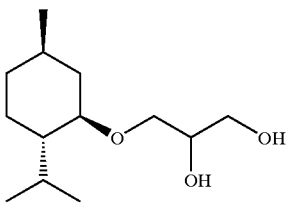

(IV)

Further, the invention relates to:

(3) a process for producing a 1-halogeno-3-1-menthoxypropan-2-ol, which comprises:

adding 1-menthol to a 1,2-epoxy-3-halogenopropane represented by the following general formula (I):

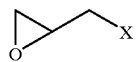
(I)

(wherein X represents a halogen atom),
in an organic solvent in the presence of a Lewis acid to produce a 1-halogeno-3-1-menthoxypropan-2-ol represented by the following general formula (II):

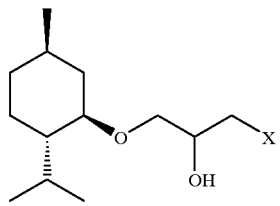
(II)

(wherein X represents a halogen atom).
And, the invention relates to:
(4) a process for producing a 1,2-epoxy-3-1-menthoxypropane, which comprises:
    epoxidating a 1-halogeno-3-1-menthoxypropan-2-ol represented by the following general formula (II):

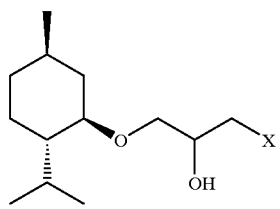
(II)

(wherein X represents a halogen atom),
with a base in the presence of a phase transfer catalyst to produce a 1,2-epoxy-3-1-menthoxypropane represented by the following chemical formula (III).

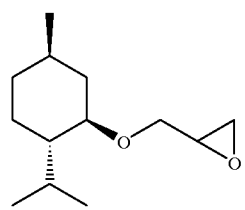
(III)

And, the invention includes:
(5) the process as in any one of the above (1) to (4), wherein X is chlorine atom in the 1,2-epoxy-3-halogenopropane represented by the above general formula (I) and the 1-halogeno-3-1-menthoxypropan-2-ol represented by the above general formula (II);
(6) the process as in the above (1) or (3), wherein the Lewis acid is at least one selected from boron trifluoride ether complex, aluminum chloride, zinc chloride, zinc bromide and ferric chloride; and
(7) the process as in the above (1), (2), (4), (5) or (6), wherein the phase transfer catalyst is a quaternary ammonium salt;
as preferred embodiments.

Furthermore, the invention relates to:

(8) a 1-halogeno-3-1-menthoxypropan-2-ol represented by the following general formula (II):

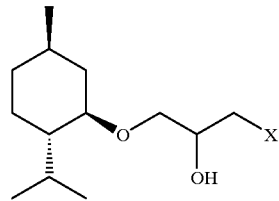
(II)

(wherein X represents a halogen atom).

And, the invention includes:

(9) 1-chloro-3-1-menthoxypropan-2-ol represented by the following chemical formula (IIa).

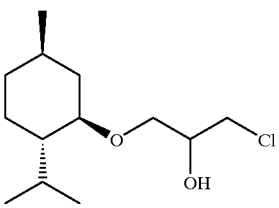
(IIa)

as a preferred embodiment.

DETAILED DESCRIPTION OF THE INVENTION

The following will explain the invention in detail.

The process of the invention for producing 3-1-menthoxypropane-1,2-diol is carried out according to the following reactions.

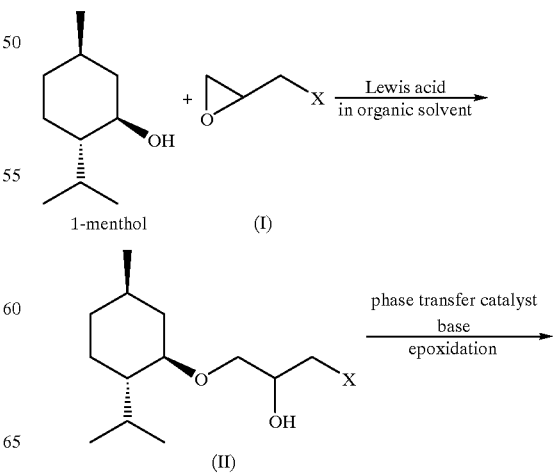

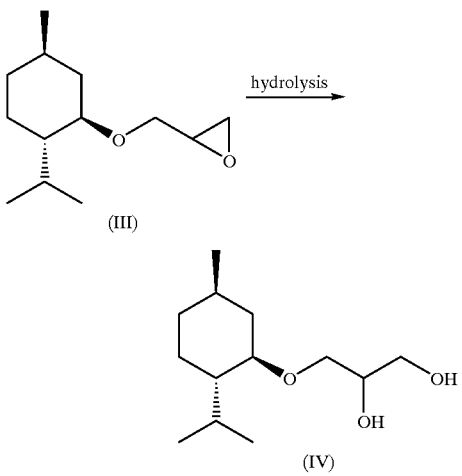

(III)

(IV)

(wherein X represents a halogen atom)

Namely, 1-menthol is added to a 1,2-epoxy-3-halogenopropane (I) in an organic solvent in the presence of a Lewis acid to produce a novel 1-halogeno-3-1-menthoxypropan-2-ol (II). Then, the 1-halogeno-3-1-menthoxypropan-2-ol (II) is epoxidated with a base in the presence of a phase transfer catalyst to produce 1,2-epoxy-3-1-menthoxypropane (III), and 3-1-menthoxypropane-1,2-diol (IV) is obtained by hydrolyzing it.

As a halogen atom X in the 1,2-epoxy-3-halogenopropane (I), fluorine atom, chlorine atom, bromine atom, iodine atom, and the like may be mentioned. Thus, specific examples of the 1,2-epoxy-3-halogenopropane include 1,2-epoxy-3-fluoropropane (epifluorohydrin), 1,2-epoxy-3-chloropropane (epichlorohydrin), 1,2-epoxy-3-bromopropane (epibromohydrin), 1,2-epoxy-3-iodopropane (epiiodohydrin), and the like. Among them, preferably used in the invention is 1,2-epoxy-3-chloropropane (epichlorohydrin) or 1,2-epoxy-3-bromopropane (epibromohydrin), the halogen atom X being chlorine atom or bromine atom, and more preferably used is 1,2-epoxy-3-chloropropane (epichlorohydrin).

Commercially available 1,2-epoxy-3-halogenopropane (I) and 1-menthol as they are can be used as starting materials.

The addition of 1-menthol to a 1,2-epoxy-3-halogenopropane (I) is necessarily carried out in an organic solvent in the presence of a Lewis acid. When a brønsted acid (protonic acid), a Grignard reagent or a base is used instead of a Lewis acid, an adduct (1-halogeno-3-1-menthoxypropane or 1,2-epoxy-3-1-menthoxypropane) is not formed or is formed only in low yields.

At the addition of 1-menthol to a 1,2-epoxy-3-halogenopropane (I), preferably adopted is the method wherein a Lewis acid is added to a solution of 1-menthol dissolved in an organic solvent, and then, a solution of 1,2-epoxy-3-halogenopropane (I) dissolved in an organic solvent is added dropwise thereto to carry out the reaction.

The molecular ratio of the 1,2-epoxy-3-halogenopropane (I) and 1-menthol to be used is preferably from about 0.8 to 2 mol, more preferably from 0.9 to 1.3 mol of 1-menthol relative to 1 mol of the 1,2-epoxy-3-halogenopropane (I).

Moreover, the amount of the Lewis acid to be used may be a similar amount to the amount of a catalyst in a conventional addition reaction, and is, in general, preferably from about 0.01 to 0.1 mol relative to 1 mol of the 1,2-epoxy-3-halogenopropane (I).

Specific examples of the Lewis acid include boron trifluoride ether complex, aluminum chloride, zinc chloride, zinc bromide, ferric chloride, and the like. One or two or more of them may be used. Among them, aluminum chloride and/or boron trifluoride ether complex are preferably used in view of good operability and economically low cost.

As the organic solvent, use is made of an organic solvent which does not affect adversely the addition of 1-menthol to a 1,2-epoxy-3-halogenopropane (I). Specific examples thereof include aliphatic hydrocarbon solvents such as hexane, heptane and octane; alicyclic hydrocarbon solvents such as cyclohexane and methylcyclohexane; aromatic hydrocarbon solvents such as benzene, toluene and xylene; petroleum ether solvents, and the like. One or two or more of them may be used. Among them, heptane and/or toluene are preferably used in view of good operability and economically low cost.

In general, the ratio of the organic solvent to be used to 1-menthol (volume/weight) is preferably from about 0.5 to 5, more preferably about 1 to 3.

The addition of 1-menthol to a 1,2-epoxy-3-halogenopropane (I) is preferably carried out under an atmosphere of an inert gas such as nitrogen gas or argon gas for smooth proceeding of the addition reaction.

Moreover, at carrying out the addition reaction by adding dropwise a solution of a 1,2-epoxy-3-halogenopropane (I) dissolved in an organic solvent to a solution of 1-menthol and a Lewis acid dissolved in an organic solvent, the time for adding the solution of the 1,2-epoxy-3-halogenopropane (I) dissolved in an organic solvent is, in general, preferably about 0.5 to 10 hours, more preferably about 1.5 to 3 hours.

The temperature for the addition reaction is preferably about 60 to 130° C., more preferably about 65 to 120° C. A 1-halogeno-3-1-menthoxypropan-2-ol (II) can be smoothly produced by the reaction for about 0.5 to 15 hours, preferably about 1 to 5 hours after completion of the addition of the organic solvent solution of a 1,2-epoxy-3-halogenopropane (I) with maintaining the above temperature.

The 1-halogeno-3-1-menthoxypropan-2-ol (II) obtained by the above addition reaction is a novel compound hitherto unknown, and is stable, usually oily, and storable.

Therefore, the 1-halogeno-3-1-menthoxypropan-2-ol (II) obtained by the above addition reaction may be stored after purification by, for example, distillation or column chromatography or without any purification, and at the production of 1,2-epoxy-3-1-menthoxypropane or 3-1-menthoxypropane-1,2-diol (IV), the compound (II) may be taken out of a storing vessel and used. Alternatively, the 1-halogeno-3-1-menthoxypropan-2-ol (II) formed by the above addition reaction may be directly used for the next epoxidation reaction without additional-treatment such as purification, after cooling according to need.

The 1-halogeno-3-1-menthoxypropan-2-ol (II) obtained by the above addition reaction is epoxydated with a base in the presence of a phase transfer catalyst to produce 1,2-epoxy-3-1-menthoxypropane (III).

As the base to be used in the epoxidation reaction, hydroxide, carbonate and/or an alkoxide of an alkali metal or alkaline earth metal may be used. Specific examples thereof include lithium hydroxide, sodium hydroxide, potassium hydroxide, calcium hydroxide, barium hydroxide, lithium carbonate, sodium carbonate, potassium carbonate, and the like. One or two or more of them may be used. Among them, sodium hydroxide and/or potassium hydroxide are preferably used.

The base is preferably added to the reaction system in the form of an aqueous solution. The concentration of the aqueous solution of the base is preferably 40% or more, especially a high concentration of 45 to 55% because of the smooth proceeding of the epoxidation reaction.

The amount of the base to be used is preferably from about 1.0 to 5.0 mol, particularly about 1.5 to 3.0 mol relative to 1 mol of the 1-halogeno-3-1-menthoxypropan-2-ol (II).

As the phase transfer catalyst to be used in the above epoxidation reaction, a quaternary ammonium salt is suitably used, and specific examples thereof include industrially easily available quaternary ammonium salts such as tetramethylammonium chloride, tetrabutylammonium bromide, tetraethylammonium iodide, tetrabutylammonium iodide, trimethylhexadecylammonium chloride, dimethyldioctylammonium chloride, trimethylbenzylammonium chloride and trioctylmethylammonium chloride. One or two or more of them may be used. Among them, trimethylbenzylammonium chloride is preferably used in view of smooth proceeding of the epoxidation reaction and economically low cost.

The amount of the phase transfer catalyst to be used is preferably from about 0.01 to 0.2 mol, particularly about 0.02 to 0.05 mol relative to 1 mol of the 1-halogeno-3-1-menthoxypropan-2-ol (II).

The above epoxidation reaction is preferably carried out in an organic solvent. As the organic solvent, there may be mentioned organic solvents which do not affect adversely the epoxidation reaction, for example, aliphatic hydrocarbon solvents such as hexane, heptane and octane; alicyclic hydrocarbon solvents such as cyclohexane and methylcyclohexane; aromatic hydrocarbon solvents such as benzene, toluene and xylene; ether solvents such as diethyl ether, diisopropyl ether, dimethoxyethane, tetrahydrofuran, dioxane and 1,3-dioxolane; petroleum ether solvents, and the like. One or two or more of them may be used. Among them, toluene and/or heptane are preferably used in view of smooth proceeding of the epoxidation reaction as well as good operability and economically low cost.

The amount of the organic solvent to be used is preferably from about 1 to 10 parts by volume, particularly about 2 to 5 parts by volume relative to 1 part by volume of the 1-halogeno-3-1-menthoxypropan-2-ol (II).

The above epoxidation reaction is preferably carried out under an atmosphere of an inert gas such as nitrogen gas or argon gas.

The temperature for the epoxidation reaction is preferably about 40 to 100° C., particularly about 50 to 80° C. 1,2-Epoxy-3-1-menthoxypropane (III) can be smoothly produced by the reaction for about 0.5 to 6 hours, preferably about 1 to 4 hours with maintaining the above temperature.

The 1,2-epoxy-3-1-menthoxypropane (III) obtained by the above epoxidation reaction is oily and storable. Therefore, the 1,2-epoxy-3-1-menthoxypropane (III) obtained by the above epoxidation reaction may be stored after purification by, for example, distillation or column chromatography or without any purification, and at the production of 3-1-menthoxypropane-1,2-diol (IV), the former compound may be taken out of a storing vessel and used. Alternatively, the 1,2-epoxy-3-1-menthoxypropane (III) obtained by the above epoxidation reaction may be directly used for the production of 3-1-menthoxypropane-1,2-diol (IV) without additional-treatment such as purification, after cooling according to need.

3-1-Menthoxypropane-1,2-diol (IV) is formed by hydrolyzing 1,2-epoxy-3-1-menthoxypropane (III) obtained by the above epoxidation reaction.

The hydrolysis of 1,2-epoxy-3-1-menthoxypropane (III) is preferably carried out in the presence of an acidic catalyst.

Examples of the acidic catalyst include mineral acids such as hydrochloric acid, sulfuric acid, nitric acid, perchloric acid and phosphoric acid; organic acids such as acetic acid, trifluoroacetic acid, trichloroacetic acid, methanesulfonic acid, trifluoromethanesulfonic acid, benzenesulfonic acid, p-toluenesulfonic acid and camphorsulfonic acid; and the like. Among them, sulfuric acid and/or perchloric acid are preferably used in view of smooth proceeding of the hydrolysis and economically low cost.

The amount of the acidic catalyst to be used is preferably from about 0.02 to 0.2 equivalent, particularly about 0.05 to 0.15 equivalent relative to 1 mol of the 1,2-epoxy-3-1-menthoxypropane (III).

The acidic catalyst is preferably added to the reaction system in the form of an aqueous solution. The concentration of the aqueous solution of the acidic catalyst is preferably about 1 to 15%.

The above hydrolysis is preferably carried out in an organic solvent. Examples of the organic solvent include ketone solvents such as acetone, methyl ethyl ketone, diethyl ketone, diisopropyl ketone, methyl tert-butyl ketone and cyclohexanone; ether solvents such as diisopropyl ether, dimethoxyethane, tetrahydrofuran, dioxane and 1,3-dioxolane; and the like. One or two or more of them may be used. Among them, acetone is preferably used in view of economically low cost.

The amount of the organic solvent to be used is preferably from about 1 to 10 parts by volume, particularly about 2 to 5 parts by volume relative to 1 part by volume of 1,2-epoxy-3-1-menthoxypropane (III).

The temperature for the above hydrolysis is preferably about 20 to 100° C., more preferably about 50 to 80° C. 3-1-Menthoxypropane-1,2-diol (IV) can be produced by the reaction for about 0.5 to 5 hours, preferably about 1 to 3 hours with maintaining the above temperature. Isolation of 3-1-menthoxypropane-1,2-diol (IV) from the reaction product containing 3-1-menthoxypropane-1,2-diol (IV) can be carried out according to a conventional method. Although the method of recovery is not particularly limited, 3-1-menthoxypropane-1,2-diol (IV) can be isolated as a concentrate, for example, in the case that a water-soluble organic solvent is used in the reaction, by adding water to the reaction mixture according to need, removing the water-soluble organic solvent used in the reaction by evaporation, adding thereto an alkaline aqueous solution and a hydrocarbon organic solvent such as hexane, butane, benzene, toluene or xylene to neutralize the acidic catalyst used and to extract 3- 1-menthoxypropane-1,2-diol (IV) with an organic solvent, and finally removing the solvent by evaporation. Purification of 3-1-menthoxypropane-1,2-diol (IV) can be effected by distillation or column chromatography.

3-1-Menthoxypropane-1,2-diol (IV) obtained as above is used for a variety of applications such as cosmetics, toiletry goods, bath agents, food and drink, medicines, and the like with making good use of the characteristics such as cooling effect, refreshing effect, odorless property and safety. Examples thereof include various lotions such as body lotion, after-shave lotion and hair-growth lotion; skin cosmetics such as washing cream, vanishing cream, cleansing cream, cold cream, emulsion, toilet water, facial mask, makeup remover and lip cream; cataplasm, plaster, nasal decongestant, antiperspirant; hair-care goods such as shampoo, rinse, treatment and conditioner; hair cosmetics such as hair tonic, hair cream and hair spray; perfumes, colognes; bath agent, body shampoo, soap; shaving foam and gel; detergents, softeners; in-door aromatic agent; tooth paste; mouth wash; ointment; food and drink such as refreshing drink, gum, candy, ice cream, sherbet, jelly, tablet, troche; and the like.

The following will explain the invention concretely with reference to Examples, but the invention is not limited at all by following Examples.

By the way, in following Examples, the instruments used for measuring or analyzing physical properties are as follows.

(1) Chemical purity

Gas chromatograph: "HP6890" manufactured by HEWLETT PACKARD

Column: "NEUTRABOND-1" manufactured by G L Science (inner diameter×length=0.25 mm×30 m)

(2) Nuclear magnetic resonance spectrum:

$^1$H-NMR: "DRX-500 type" (500 MHz) manufactured by Bruker (3) Infrared absorption spectrum:

Instrument: "Nicolet AVATAR 360" manufactured by Nicolet Japan K.K.

Measuring method: NaCl film method (4) Mass spectrum (MS):

M-80 mass spectrometer: manufactured by Hitachi Ltd. (ionization voltage, 20 eV)

(5) Polarimeter:

DIP-360 manufactured by Nihon Bunko K.K.

EXAMPLE 1

Synthesis of 1-chloro-3-1-menthoxypropan-2-ol (1) Under a nitrogen atmosphere, into a reaction flask (volume: 500 ml) were added 1-menthol (manufactured by Takasago International Corporation) (136.7 g, 0.8763 mol) and n-heptane (295 ml), and the whole was dissolved at room temperature. Next, anhydrous aluminum chloride (3.5 g, 26.88 mmol) was added thereto and dissolved under stirring, and then the temperature was raised to 70° C. Into the solution was added dropwise epichlorohydrin (61 g, 0.6572 mol) at the same temperature over a period of 2 hours. After the addition, they were reacted at the same temperature for 7 hours. Thereafter, the reaction mixture was cooled to room temperature.

(2) The reaction mixture obtained in the above (1) was washed with water and then washed with a 10% aqueous sodium carbonate solution, and removal of n-heptane by evaporation afforded an oily substance. The oily substance was distilled under reduced pressure to recover unreacted 1-menthol (57.2 g, 0.37 mol) at a boiling point of 78 to 99° C./600 Pa (4.5 mmHg) and further to obtain 1-chloro-3-1-menthoxypropan-2-ol (117 g) (chemical purity: 97.8%) as a colorless oily substance (yield: 70% based on epichlorohydrin).

(3) The analytical results of 1-chloro-3-1-menthoxypropan-2-ol obtained in the above (2) were as follows:

$[\alpha]_d^{25}$: −73.7 (c=1.05, EtOH)

MS (m/e, %): 248 (M$^+$), 165, 163, 139, 138, 123, 109, 97, 95, 83, 81, 71, 69, 57, 55, 53, 43, 41, 29, 27.

IR (neat, cm$^{-1}$) : 3422, 2955, 2922, 2869, 1456, 1385, 1370, 1344, 1180, 1114, 1067, 1050, 1011, 991, 974, 922, 845, 753.

$^1$H-NMR (CDCl$_3$; δ ppm): 0.78 (3H, d, J=6.9), 0.81–0.88 (2H, m), 0.90 (3H, d, J=7.0), 0.93 (3H, d, J=6.5), 0.96–1.01 (1H, m), 1.20–1.26 (1H, m), 1.30–1.40 (1H, broad), 1.61–1.66 (2H, m), 2.09 (1H, m), 2.14 (1H, m), 2.52 (1H, d, J=5.9), 3.09 (1H, dt, J=10.6, 4.1), 3.44 (1H, dd, J=9.4, 5.2), 3.60 (1H, dd, J=11.0, 5.6), 3.73 (1H, dd, J=9.4, 5.2), 3.91–3.97 (1H, m).

EXAMPLES 2 TO 5 AND COMPARATIVE EXAMPLES 1 TO 4

Synthesis of 1-chloro-3-1-menthoxypropan-2-ol (1) As Examples 2 to 5, 1-chloro-3-1-menthoxypropan-2-ol was produced in a similar manner to Example 1 with the exception that each Lewis acid shown in following Table 1 was used in the same amount (26.88 mmol) as that in Example 1. The yields were all 65% or more as shown in Table 1.

(2) On the other hand, 1-chloro-3-1-menthoxypropan-2-ol was produced in a similar manner to Example 1 with the exception that, as Comparative Examples 1 to 3, brønsted acids (protonic acids) [sulfuric acid (H$_2$SO$_4$) (Comparative Example 1), phosphoric acid (85% H$_3$PO$_4$) (Comparative Example 2), and p-toluenesulfonic acid (monohydrate) (Comparative Example 3)] instead of the Lewis acid, and, as Comparative Example 4, a Grignard reagent (ethylmagnesium chloride: EtMgCl) instead of the Lewis acid were used each in the same amount (26.88 mmol) as that in Example 1. The yields were as shown in Table 1.

COMPARATIVE EXAMPLE 5

Synthesis of 1-chloro-3-1-menthoxypropan-2-ol

Under a nitrogen atmosphere, into a reaction flask (volume: 300 ml) were added 1-menthol (10 g, 64.1 mmol) and toluene (50 ml), and the whole was dissolved at room temperature and then the inner temperature was lowered to 5° C. by ice-cooling. Thereafter, 60% sodium hydride (2.82 g, 70.5 mmol) was added thereto and then the temperature was raised to 100° C. Into the solution was added dropwise epichlorohydrin (5.93 g, 64.1 mmol) over a period of 1 hour. After the addition, they were reacted at the same temperature for 3 hours, but the adducts (1-chloro-3-1-menthoxypropan-2-ol or 1,2-epoxy-3-1-menthoxypropane) were not formed at all.

TABLE 1

| | Catalyst | Yield |
|---|---|---|
| Example 1 | AlCl$_3$ | 70.0% |
| Example 2 | ZnBr$_2$ | 66.8% |
| Example 3 | FeCl$_3$ | 67.6% |
| Example 4 | ZnCl$_2$ | 72.5% |
| Example 5 | (C$_2$H$_5$)$_2$O.BF$_3$ | 65.7% |
| Comparative Example 1 | H$_2$SO$_4$ | 9.6% |
| Comparative Example 2 | 85% H$_3$PO$_4$ | 14.8% |
| Comparative Example 3 | p-toluenesulfonic acid.H$_2$O | 4.0% |
| Comparative Example 4 | EtMgCl | 32.9% |
| Comparative Example 5 | note[1] | —[2] |

[1]NaH was used
[2]No adducts (1-chloro-3-1-menthoxypropan-2-ol or 1,2-epoxy-3-1-menthoxypropane) were formed.

As apparent from the results of Examples 1 to 5 shown in above Table 1, 1-chloro-3-1-menthoxypropan-2-ol was obtainable in high yields of 65% or more by carrying out the reaction with Lewis acids [aluminum chloride (AlCl$_3$), zinc bromide (ZnBr$_2$), ferric chloride (FeCl$_3$), zinc chloride (ZnCl$_2$), boron trifluoride ether complex ((C$_2$H$_5$)$_2$O.BF$_3$)].

On the other hand, as shown in the results of Comparative Examples 1 to 3, in the cases that brønsted acids (protonic acids) [sulfuric acid (H$_2$SO$_4$) (Comparative Example 1), phosphoric acid (85% H$_3$PO$_4$) (Comparative Example 2), and p-toluenesulfonic acid (monohydrate) (Comparative Example 3)] were used as catalysts instead of the Lewis acid, 1-chloro-3-1-menthoxypropan-2-ol was formed but the yields were 9.6%, 14.8%, and 4.0%, respectively, which were lower than those in Examples 1 to 5.

Moreover, as shown in the result of Comparative Example 4, in the case that a Grignard reagent [ethylmagnesium chloride (EtMgCl)] was used as the catalyst instead of the Lewis acids, 1-chloro-3-1-menthoxypropan-2-ol was formed but the yield was 32.9%, which was substantially lower that those in Examples 1 to 5.

Furthermore, as is apparent from the result of Comparative Example 5, when the addition of 1-menthol to epichlorohydrin was carried out using a base (sodium hydride), no adducts (1-chloro-3-1-menthoxypropan-2-ol or 1,2-epoxy-3-1-menthoxypropane) were formed.

As is apparent from the above results, in the case of the process of the invention where the addition of 1-menthol to epichlorohydrin was carried out in the presence of a Lewis acid, a novel compound of 1-chloro-3-1-menthoxypropan-2-ol can be obtained smoothly in high yields.

EXAMPLE 6

Synthesis of 1,2-epoxy-3-1-menthoxypropane (1) Under a nitrogen atmosphere, into a reaction flask (volume: 200 ml) were added 1-chloro-3-1-menthoxypropan-2-ol (50 g, chemical purity: 97.8%, 0.1968 mol) obtained in Example 1, toluene (75 ml), a 50% aqueous sodium hydroxide solution (31.49 g, 0.3936 mol) and a 50% aqueous benzyltrimethylammonium chloride solution (1.46 g, 4.26 mmol), and they were reacted at 75° C. for 2 hours. After completion of the reaction, the organic layer was washed with water and then the solvent (toluene) was removed to obtain an oily substance. The oily substance was distilled under reduced pressure to obtain 1,2-epoxy-3-1-menthoxypropane (34.6 g, chemical purity: 98.25%) [boiling point: 75–80° C./10.7 Pa (0.08 mmHg)] as a colorless transparent oily substance (yield: 97.0% based on 1-chloro-3-1-menthoxypropan-2-ol).

(2) The analytical results of 1,2-epoxy-3-1-menthoxypropane obtained in the above (1) were as follows:

$[\alpha]_D^{25}$: −90.95° (c=1.05, EtOH)

MS (m/e, %): 212 (M$^+$), 155, 138, 127, 123, 109, 95, 81, 71, 69, 67, 57, 55, 43, 41, 31, 29, 27.

IR (neat, cm$^{-1}$): 3050, 2960, 2925, 2875, 1460, 1370, 1095, 910, 845, 765.

$^1$H-NMR (CDCl$_3$; δ ppm) : 0.78 (3H, d, J=6.9), 0.81–0.88 (2H, m), 0.90 (3H, d, J=7.0), 0.92 (3H, d, J=6.6), 0.95–1.00 (1H, m), 1.24 (1H, m), 1.36 (1H, m), 1.59–1.67 (2H, m), 2.08 (1H, m), 2.14 (1H, m), 2.38 (1H, broad), 3.06–3.12 (1H, m), 3.38–3.44 (1H,m), 3.57–3.66 (2H, m), 3.71–3.75 (1H, dd), 3.90–3.96 (1H, m).

EXAMPLE 7 AND COMPARATIVE EXAMPLE 6

Synthesis of 1,2-epoxy-3-1-menthoxypropane (1) As Example 7, 1,2-epoxy-3-1-menthoxypropane was synthesized in a similar manner to Example 6 with using benzyltrimethylammonium chloride as the phase transfer catalyst and changing the reaction time. The conversion of 1-chloro-3-1-menthoxypropan-2-ol at each reaction time and the selectivity to 1,2-epoxy-3-1-menthoxypropane were as shown in following Table 2.

(2) As Comparative Example 6, 1,2-epoxy-3-1-menthoxypropane was synthesized in a similar manner to Example 6 with the exception that a phase transfer catalyst (benzyltrimethylammonium chloride) was not added, with changing the reaction time. The conversion of 1-chloro-3-1-menthoxypropan-2-ol at each reaction time and the selectivity to 1,2-epoxy-3-1-menthoxypropane were as shown in following Table 2.

TABLE 2

| Reaction Time (hr) | Example 7 (Phase transfer catalyst) | | Comparative Example 6 (Phase transfer catalyst was not used) | |
|---|---|---|---|---|
| | Conversion (%) | Selectivity (%) | Conversion (%) | Selectivity (%) |
| 2 | 98.2 | 98.8 | 86.3 | 98.2 |
| 3 | 99.7 | 98.5 | 90.5 | 97.1 |
| 4 | 100 | 98.2 | 93.0 | 97.1 |
| 5 | — | — | 95.2 | 97.5 |
| 6 | — | — | 96.8 | 97.3 |
| 7 | — | — | 98.3 | 98.4 |
| 8 | — | — | 99.1 | 97.4 |
| 9 | — | — | 99.4 | 96.9 |

As is apparent from the results shown in Table 2, in Example 7 wherein the reaction was carried out with using a phase e transfer catalyst, at the reaction time of 4 hours, the conversion of 1-chloro-3-1-menthoxypropan-2-ol reached 100% and the selectivity to 1,2-epoxy-3-1-menthoxypropane is 98.2% which is an extremely high value.

On the other hand, in Comparative Example 6 wherein the reaction was carried out with adding no phase transfer catalyst, increase of the conversion remarkably diminished after 2 hours of the reaction, and thus, at the reaction time of 9 hours, the conversion of 1-chloro-3-1-menthoxypropan-2-ol reached barely 99.4%. At that time, however, the selectivity to 1,2-epoxy-3-1-menthoxypropane decreased to 96.9%.

From these results, it is evident that the process of the invention wherein epoxidation of 1-halogeno-3-1-menthoxypropan-2-ol to 1,2-epoxy-3-1-menthoxypropane is carried out with using a phase transfer catalyst is extremely effective.

EXAMPLE 8

Synthesis of 3-1-menthoxypropane-1,2-diol (1) Under a nitrogen atmosphere, into a reaction flask (volume: 3 liters) were added 1-menthol (manufactured by Takasago International Corporation) (300 g, 1.923 mol) and toluene (616 ml), and the whole was dissolved at room temperature. Then, anhydrous aluminum chloride (20.5 g, 0.154 mol) was added thereto and dissolved under stirring, and the temperature was raised to 116° C. Into the solution was added dropwise a solution of epichlorohydrin (178 g, 1.923 mol) dissolved in toluene (366 ml) over a period of 2 hours. After the addition, they were reacted at the same temperature for 1 hour. Thereafter, the reaction mixture was cooled to 50° C.

(2) Under a nitrogen atmosphere, into the reaction mixture obtained in the above (1) were added a 50% aqueous sodium hydroxide solution (354 g, 3.846 mol) and a 50% aqueous benzyltrimethylammonium chloride solution (14.4 g), and they were reacted at 75° C. for 2 hours. After completion of the reaction, the mixture was washed with water (513 g) and then the solvent was removed by evaporation to obtain an oily substance. The substance was distilled under reduced pressure to obtain 1,2-epoxy-3-1-menthoxypropane (250 g) [boiling point: 125–140°

C./1200 Pa (9 mmHg)] as a colorless transparent oily substance (yield: 61.3% based on epichlorohydrin).

(3) Under a nitrogen atmosphere, into a reaction flask (volume: 3 liters) were added 1,2-epoxy-3-1-menthoxypropan (245 g, 1.156 mol) obtained in the above (2), acetone (500 ml), and 3% aqueous sulfuric acid (235 g), and the whole was dissolved under stirring, followed by heating under reflux for 2 hours. Next, water (1000 ml) was added thereto and then, acetone was removed by evaporation under reduced pressure. Thereafter, a 3% aqueous sodium hydroxide solution (800 ml) and toluene (850 ml) was added thereto and after separation of the organic layer, the solvent was removed by evaporation to obtain an oily substance. The substance was distilled under reduced pressure to obtain 3-1-menthoxypropane-1,2-diol (250 g, chemical purity: 98.7%) [boiling point: 120–140° C./40 Pa (0.3 mmHg)] as a colorless transparent oily substance.

According to the process of the invention, 3-1-menthoxypropane-1,2-diol useful as a cooling agent or a refrigerant can be produced safely and in high yields with a high purity through simple operations without using metal sodium, sodium hydride, a peroxide, or the like which is unstable and has an danger of explosion, and thus the process is industrially advantageous.

Moreover, according to the invention, a 1-halogeno-3-1-menthoxypropan-2-diol which is a novel intermediate for producing 3-1-menthoxypropane-1,2-diol can be produced through simple operations, safely and in high yields with a high purity by adding 1-menthol to a 1,2-epoxy-3-halogenopropane in an organic solvent in the presence of a Lewis acid without using metal sodium, sodium hydride, a peroxide, or the like.

Furthermore, according to the invention, 1,2-epoxy-3-1-menthoxypropane which is an intermediate for 3-1-menthoxypropane-1,2-diol can be produced safely and in high yields with a high purity through a simple operation of epoxidating the novel intermediate of a 1-halogeno-3-1-menthoxypropan-2-diol with a base in the presence of a phase transfer catalyst.

And, the novel 1-halogeno-3-1-menthoxypropan-2-diol of the invention is useful as an intermediate for producing 3-1-menthoxypropane-1,2-diol.

While the invention has been described in detail and with reference to specific embodiments thereof, it will be apparent to one skilled in the art that various changes and modifications can be made therein without departing from the spirit and scope thereof.

This application is based on Japanese patent application No. 2000-322287, filed Oct. 23, 2000, the entire contents thereof being hereby incorporated by reference.

What is claimed is:

1. A process for producing 3-1-menthoxypropane-1,2-diol, which comprises:

adding 1-menthol to a 1,2-epoxy-3-halogenopropane represented by the following general formula (I):

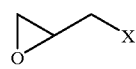

(I)

(wherein X represents a halogen atom), in an organic solvent in the presence of a Lewis acid to produce a 1-halogeno-3-1-menthoxypropan-2-ol represented by the following general formula (II):

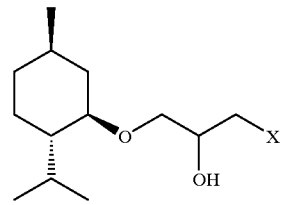

(II)

(wherein X represents a halogen atom), then, epoxidating it with a base in the presence of a phase transfer catalyst to produce a 1,2-epoxy-3-1-menthoxypropane represented by the following chemical formula (III):

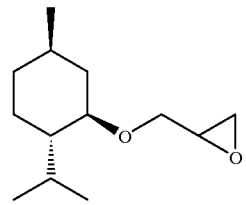

(III)

and further hydrolyzing it to produce 3-1-menthoxypropane-1,2-diol represented by the following chemical formula (IV)

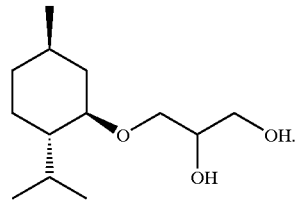

(IV)

2. A process for producing 3-1-menthoxypropane-1,2-diol, which comprises:

epoxidating a 1-halogeno-3-1-menthoxypropan-2-ol represented by the following general formula (II):

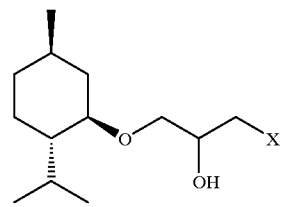

(II)

(wherein X represents a halogen atom), with a base in the presence of a phase transfer catalyst to produce a 1,2-epoxy-3-1-menthoxypropane represented by following chemical formula (III):

(III)

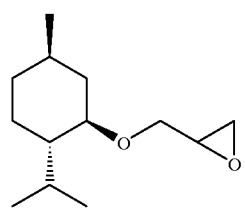

and further hydrolyzing it to produce 3-1-menthoxypropane-1,2-diol represented by the following chemical formula (IV)

(IV)

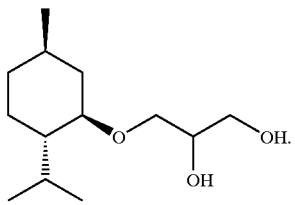

3. A process for producing a 1-halogeno-3-1-menthoxypropan-2-ol, which comprises:

adding 1-menthol to a 1,2-epoxy-3-halogenopropane represented by the following general formula (I):

(I)

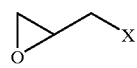

(wherein X represents a halogen atom), in an organic solvent in the presence of a Lewis acid to produce a 1-halogeno-3-1-menthoxypropan-2-ol represented by the following general formula (II):

(II)

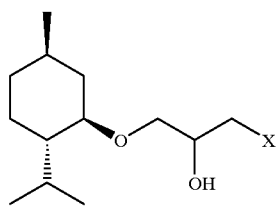

(wherein X represents a halogen atom).

4. A process for producing a 1,2-epoxy-3-1-menthoxypropane, which comprises:

epoxidating a 1-halogeno-3-1-menthoxypropan-2-ol represented by the following general formula (II):

(II)

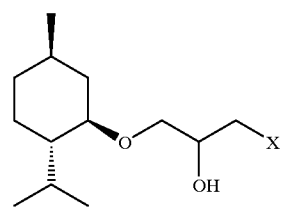

wherein X represents a halogen atom), with a base in the presence of a phase transfer catalyst to produce a 1,2-epoxy-3-1-menthoxypropane represented by the following chemical formula (III):

(III)

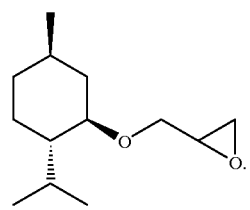

5. The process according to any one of claims 1 to 4, wherein X is chlorine atom in the 1,2-epoxy-3-halogenopropane represented by the above general formula (I) and the 1-halogeno-3-1-menthoxypropan-2-ol represented by the above general formula (II).

6. The process according to claim 1 or 3, wherein the Lewis acid is at least one selected from boron trifluoride ether complex, aluminum chloride, zinc chloride, zinc bromide and ferric chloride.

7. The process according to claim 1, 2 or 4, wherein the phase transfer catalyst is a quaternary ammonium salt.

8. The process according to any one of claims 1, 2 or 4, wherein X is chlorine atom in the 1,2-epoxy-3-halogenopropane represented by the above general formula (1) and the 1-halogeno-3-1-menthoxypropane-2-ol represented by the above general formula (II), and, wherein the phase transfer catalyst is a quaternary ammonium salt.

9. The process according to claim 1, wherein the phase transfer catalyst is a quaternary ammonium salt and wherein the Lewis acid is at least one selected from boron trifluoride ether complex, aluminum chloride, zinc chloride, zinc bromide and ferric chloride.

10. A 1-halogeno-3-1-menthoxypropan-2-ol represented by the following general formula (II):

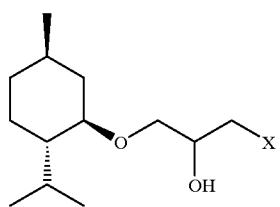
(II)
(wherein X represents a halogen atom).
11. 1-Chloro-3-1-menthoxypropan-2-ol represented by the following chemical formula (IIa):
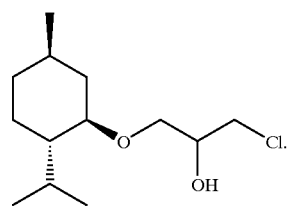
(IIa)
* * * * *

UNITED STATES PATENT AND TRADEMARK OFFICE
CERTIFICATE OF CORRECTION

PATENT NO.   : 6,407,293 B1
DATED        : June 18, 2002
INVENTOR(S)  : Akira Amano et al.

It is certified that error appears in the above-identified patent and that said Letters Patent is hereby corrected as shown below:

Title page, Item [54] and Column 1, line 2,
Title, "3-1-MENTHOXYPROPANE-1,2-DIOL" should read
-- 3-L-MENTHOXYPROPANE-1,2-DIOL --.

Item [75], Inventors, "Akira Amano; Teruyoshi Akiyama; Takashi Miura; Toshimitsu Hagiwara, all of Kanagawa (JP)" should read -- Akira Amano; Teruyoshi Akiyama; Takashi Miura; Toshimitsu Hagiwara, all of Hiratsuka (JP) --.

Column 1,
Line 20, "have" should read -- has --.

Column 2,
Line 51, "much less" should read -- and furthermore, --; and
Line 56, "Other" should read -- Another --.

Column 8,
Line 51, "additional-treatment" should read -- additional treatment --; and
Line 54, "epoxydated" should read -- epoxidated --.

Column 9,
Line 61, "additional-treatment" should read -- additional treatment --.

Column 13,
Line 46, "6 ppm)" should read -- $\delta$ ppm) --.

Column 14,
Line 23, "phase e" should read -- phase --.

Column 15,
Line 66, "1-menthoxypropan-2-ol" should read -- 1-menthoxypropane-2-ol --.

Column 16,
Line 49, "1-halogeno-3-1-menthoxypropan-2-ol" should read -- 1-halogeno-3-1-menthoxypropane-2-ol --.

UNITED STATES PATENT AND TRADEMARK OFFICE
CERTIFICATE OF CORRECTION

PATENT NO.    : 6,407,293 B1
DATED         : June 18, 2002
INVENTOR(S)   : Akira Amano et al.

It is certified that error appears in the above-identified patent and that said Letters Patent is hereby corrected as shown below:

Column 17,
Line 30, "menthoxypropan-2-ol" should read -- menthoxypropane-2-ol --;
Line 43, "1-menthoxypropan-2-ol" should read -- 1-menthoxypropane-2-ol --; and
Line 66, "1-halogeno-3-1-menthoxypropan-2-ol" should read -- 1-halogeno-3-1-menthoxypropane-2-ol --.

Column 18,
Line 35, "1-halogeno-3-1-menthoxypropan-2-ol" should read -- 1-halogeno-3-1-menthoxypropane-2-ol"; and
Line 66, "1-halogeno-3-1-menthoxypropan-2-ol" should read -- 1-halogeno-3-1-menthoxypropane-2-ol --.

Column 19,
Line 15, "1-Chloro-3-1-menthoxypropan-2-ol" should read -- 1-Chloro-3-1-menthoxypropane-2-ol --.

Signed and Sealed this

Tenth Day of December, 2002

JAMES E. ROGAN
*Director of the United States Patent and Trademark Office*